US008535693B2

(12) United States Patent
Chaniyilparampu et al.

(10) Patent No.: US 8,535,693 B2
(45) Date of Patent: Sep. 17, 2013

(54) TOPICAL FORMULATION(S) FOR THE TREATMENT OF INFLAMMATION, SKIN AND MUCOSAL DISORDERS AND OTHER DISEASES THEREOF

(75) Inventors: Ramchand Nanappan Chaniyilparampu, Vijayawada (IN); Madhavi Mungala, Vijayawada (IN); Anuj Kapoor, Vijayawada (IN); Ganga Raju Gokaraju, Vijayawada (IN); Rama Raju Gokaraju, Vijayawada (IN); Kiran Bhupathiraju, Vijayawada (IN); Trimurtulu Golakoti, Vijayawada (IN); Anitha Krishnan Nair, Vijayawada (IN); Malliga Raman Murali, Vijayawada (IN); Kavitha Parthasarathy, Vijayawada (IN)

(73) Assignee: Laila Pharmaceuticals Private Limited, Vijayawada, IN (US)

( * ) Notice: Subject to any disclaimer, the term of this patent is extended or adjusted under 35 U.S.C. 154(b) by 0 days.

(21) Appl. No.: 13/132,155

(22) Filed: Jun. 1, 2011

(65) Prior Publication Data
US 2012/0052095 A1    Mar. 1, 2012

Related U.S. Application Data

(63) Continuation of application No. PCT/IN2009/000689, filed on Nov. 30, 2009.

(30) Foreign Application Priority Data

Dec. 1, 2008    (IN) .......................... 3007/CHE/2008

(51) Int. Cl.
    *A61K 9/00*    (2006.01)
(52) U.S. Cl.
    USPC ........................................................ 424/400
(58) Field of Classification Search
    None
    See application file for complete search history.

(56) References Cited

U.S. PATENT DOCUMENTS

| | | | | |
|---|---|---|---|---|
| 6,444,647 | B1 * | 9/2002 | Robinson et al. | 514/18.6 |
| 6,492,326 | B1 * | 12/2002 | Robinson et al. | 514/18.6 |
| 7,098,189 | B2 * | 8/2006 | Malik | 514/25 |
| 7,608,642 | B2 * | 10/2009 | Malik | 514/573 |
| 7,776,915 | B2 * | 8/2010 | Morariu | 514/558 |
| 7,968,115 | B2 * | 6/2011 | Kurzrock et al. | 424/450 |
| 2004/0009200 | A1 | 1/2004 | Seyler et al. | |
| 2004/0116511 | A1 * | 6/2004 | Malik | 514/453 |
| 2004/0126442 | A1 | 7/2004 | Quintanilla Almagro et al. | |
| 2005/0008588 | A1 * | 1/2005 | Candau et al. | 424/59 |
| 2006/0067998 | A1 * | 3/2006 | Kurzrock et al. | 424/450 |
| 2006/0216251 | A1 * | 9/2006 | Morariu | 424/59 |
| 2007/0243132 | A1 * | 10/2007 | Russell-Jones et al. | 424/1.11 |
| 2007/0292461 | A1 * | 12/2007 | Tamarkin et al. | 424/401 |
| 2008/0138400 | A1 * | 6/2008 | Kurzrock et al. | 424/450 |
| 2008/0138417 | A1 | 6/2008 | Grigsby | |
| 2008/0160077 | A1 * | 7/2008 | Borowy-Borowski | 424/456 |
| 2009/0252796 | A1 | 10/2009 | Mazed et al. | |
| 2010/0272790 | A1 * | 10/2010 | Morariu | 424/450 |
| 2011/0033525 | A1 * | 2/2011 | Liu | 424/450 |
| 2011/0206739 | A1 * | 8/2011 | Nicolosi et al. | 424/400 |
| 2012/0121696 | A1 * | 5/2012 | Liu | 424/450 |

FOREIGN PATENT DOCUMENTS

| | | | |
|---|---|---|---|
| WO | WO 0101816 A1 * | 1/2001 | |
| WO | 0224152 A | 3/2002 | |
| WO | 03888986 A | 10/2003 | |
| WO | 2007043058 A | 4/2007 | |
| WO | 2009121069 A | 10/2009 | |
| WO | WO 2009121069 A2 * | 10/2009 | |
| WO | WO 2010010431 A1 * | 1/2010 | |
| WO | 2010070664 A | 6/2010 | |
| WO | WO 2010070665 A2 * | 6/2010 | |

OTHER PUBLICATIONS

Bisht, S.; Feldmann, G.; Soni, S.; Ravi, R.; Karikar, C; Maitra, A.; Maitra, A., Polymericnanoparticle-encapsulated curcumin ("nanocurcumin"): a novel strategy for human cancer therapy. J. Nanobiotechnol. 2007, 5, (3), 1-18.*
Wang et al., Enhancing anti-inflammation activity of curcumin through O/W nanoemulsions. Food Chemistry, May 15, 2008, vol. 108, Iss 2, pp. 419-424.
Aggarwal et al., Anticancer Potential of Curcumin: Preclinical and Clinical Studies, Anticancer Research, 2003. vol. 23, pp. 363-398.
Heng et al., "Drug-induced suppression of phosphorylase kinase activity correlates with resolutionof psoriasis as assessed by clinical, histological and immunohistochemichal parameters". British Journal of Dermatology, vol. 143. No. 5, 2000, pp. 937-949.
Otte et al., "Nictinamide-Biologic actions of an emerging cosmetic ingredient". International Journal of Cosmetic Science, vol. 27, No. 5, Oct. 2005, pp. 255-261.
Supplementary European Search Report dated Jun. 26, 2012, issued for EP 09833084.
Mason et al., Nanoemulsions: formation, structure, and physical properties. Journal of Physics: Condensed Matter 18 (2006) R635-R666.

* cited by examiner

*Primary Examiner* — Robert A Wax
*Assistant Examiner* — Olga V Tcherkasskaya
(74) *Attorney, Agent, or Firm* — Kramer Amado, P.C.

(57) ABSTRACT

Nanoemulsified topical formulation comprising curcumin, tetrahydroxycurcumin (BDMC) and curcuminoid either alone or in combinations in an amount of 0.001% to 50% together with one or more pharmaceutically, nutraceutically or dietically acceptable excipient(s) or inactive ingredients, useful for the treatment of inflammation, various skin and oral disorders, mucosal disorders and other diseases associated or related thereof.

21 Claims, 11 Drawing Sheets

TOPICAL FORMULATION(S) FOR THE TREATMENT OF INFLAMMATION, SKIN AND MUCOSAL DISORDERS AND OTHER DISEASES THEREOF

CROSS REFERENCE TO RELATED APPLICATIONS

This application is a continuation of International Patent Application PCT/IN2009000689 entitled "Topical Formulation(s) for the Treatment of Inflammation, Skin and Mucosal Disorders and other Diseases Thereof," filed on Nov. 30, 2009 and published as WO 2010/070675 on Jun. 24, 2010. International Patent Application PCT/IN2009000689 is incorporated by reference herein.

TECHNICAL FIELD

The present invention relates to nanoemulsified topical formulation(s) comprising curcumin, tetrahydroxycurcumin/Bis-O-Demethyl curcumin (BDMC) or curcuminoids either alone or in combinations, useful for the treatment of inflammation, oral disorders various skin disorders, mucositic disorders and other diseases thereof.

BACKGROUND OF THE INVENTION

Human Skin is composed of three primary layers: the epidermis, which provides waterproofing and serves as a barrier to infection; the dermis, which serves as a location for the appendages of skin; and the hypodermis, which is called the basement membrane.

Skin disorder is related to epidermis, the outermost layer of the skin. It can be due to bacterial, viral, or fungal infections. Skin disorders can be a sign of imbalance in the body system.

Psoriasis is a non-contagious disorder which affects the skin and joints. The scaly patches caused by psoriasis, called psoriatic plaques, are areas of inflammation and excessive skin production. This disorder is a chronic recurring condition which varies in severity from minor localised patches to complete body coverage. There are many treatments available, but because of its chronic recurrent nature, psoriasis is a challenge to treat.

Pathophysiologically, one component of psoriasis not often focused upon is the presence of a defective skin barrier in psoriasis. Because of the rapid epidermal turnover, replacing the epidermis once every 4 days in active psoriasis, psoriatic patients possess a defective skin barrier with barrier function resembling that of the jellyfish. In contrast in normal skin, the epidermis is replaced once every 28-30 days. This result in stratum corneum which has a much better barrier function that does not allow water to escape or chemicals and bacteria to penetrate. The body is thus better protected from further injury and infection.

Psoriasis, skin wounds, acne, burns, eczema, and smoking-induced injuries are important pathological conditions of skin. Although many treatments currently exist for these conditions, there is a need for more effective treatments, particularly in dealing with superficial bacterial overgrowth by *Staphylococcus aureus* in conjunction with some of these conditions.

These conditions are frequently accompanied by inflammation, which can be mediated by a number of inflammatory cytokines secreted by inflammatory cells such as lymphocytes and macrophages, and by a number of locally or regionally acting substances, such as histamine, bradykinin, serotonin, the prostaglandins, thromboxanes, leukotrienes, and platelet-activating factor. However, these conditions share the same platform or pathological mechanism that is inflammation. Particularly, understanding the important inflammatory mechanism will help to understand the basis for psoriasis and the association of inflammatory diseases and other conditions in order to develop more effective treatments for skin damages such as wounds, burns, eczemas and acne.

In non-psoriatic subjects, inflammation can also be induced by a variety of infectious or allergic stimuli in diseases such as acne and eczemas, as well as by a variety of physical and chemical stimuli, such as burns, wounds, smoking/nicotine-induced injury and sun-induced skin damage leading to premature aging. These non-psoriatic inflammatory lesions also show increased levels of phosphorylase kinase. The increased glycogen breakdown resulting from increased activity of phosphorylase kinase ensures increased ATP stores for the multiple energy-dependent processes in the inflammatory cascade in these conditions.

In spite of clear biochemical and genetic origins of psoriasis as well as the pathology of acne, eczemas, burns, wounds, smoking/nicotine-induced injury, sun-induced skin damage and premature aging, and other conditions causing damage to the tissues through inflammation, there is still a need for more effective pharmaceutical compositions as well as effective treatments for psoriasis, acne, eczemas, wounds, burns, smoking/nicotine-induced damage, sun-induced damage and premature aging, as well as other conditions causing damage to the tissues through inflammation. In particular, there is a need for effective compositions as well as treatments that can reduce inflammation on the target site and those that are effective in situations in which there is bacterial overgrowth, as well as a need for treatments that can decrease the excessive scar tissue and detrimental proliferative response to skin and blood vessels in response to injury. In particular, smoking and sun-induced inflammatory damage can also promote premature aging. Inhibition of inflammation in these conditions, i.e., by inhibition of phosphorylase kinase activity, may prevent premature aging in sun-damaged skin and in the skin of chronic smokers. The timely treatment of burns and scalds by phosphorylase kinase inhibitors may decrease or prevent the development of excessive scarring.

There are many synthetic drug products available in market for treatment of psoriasis however, because of its chronic recurrent nature; psoriasis is a challenge to treat.

U.S. Pat. No. 6,515,016 describes a method for treating or preventing psoriasis, comprising administering to a patient in need thereof a therapeutically effective amount of an anti-microtubule agent, wherein said anti-microtubule agent is paclitaxel, or an analogue or derivative thereof.

U.S. Pat. No. 6,107,349 discloses a method for treating psoriasis in a human patient comprising administering to said patient by oral ingestion on a continuing basis therapeutic amounts in combination of Vitamin E evening primrose oil, folic acid and B-complex vitamins selected from the group consisting of Vitamin B-1, Vitamin B-2 Vitamin 3, Vitamin B-6, Vitamin B-12, biotin, para amino benzoic acid and lipotropic factors.

U.S. Pat. No. 6,830,758 claims a water insoluble, protective, adhesive skin patch useful for treating or preventing psoriasis, dermatitis, and/or eczema.

Further, there is ample literature available on herbal compositions for the treatment of psoriasis. WO/2003/057133 provides a novel herbal composition containing the extracts of the leaves and/or stem of *Argemone mexicana* plant, optionally containing the extract of the fruits of *Cuminum cyminum*, which exhibits useful in vitro, in vivo and interesting immunological and pharmacological activities; a process for preparation thereof; and a method of treatment of psoriasis and related immunological and biological disorders by administration of the said novel herbal composition.

U.S. Pat. No. 5,925,376 describes a method for inhibiting proliferation and terminal differentiation of psoriatic epidermal cells comprising the step of contacting the psoriatic epidermal cells with curcumin administered in a dose and by a route selected from the group consisting of (a) oral administration from 250 mg to 2 g daily and (b) a topical semi solid dosage forms, ointment/cream/gel/lotions in the concentration of 0.1% to 10%, together with one to four additional compounds, each additional compound being selected from the group consisting of: (i) 1-alpha,25-dihydroxy vitamin D3 in the form of 0.005% ointment; (ii) etretinate administered in a dose of 25 mg from one to three times daily; (iii) diltiazem administered at a dose of 60 mg three times daily; and (iv) anthralin administered in an ointment or paste in a concentration of from about 0.1% to about 3% once or twice daily. v) collagen administered as an ointment/cream/gel.

US20080058426 describes a cream composition containing a mixture of tetrahydrocurcuminoids comprising 70-80% tetrahydrocurcumin, 15-20% tetrahydrodemethoxycurcumin, and 2.5-6.5% tetrahydrobisdemethoxycurcumin.

Curcumin has been found to be a selective phosphorylase kinase inhibitor (Reddy S, Aggarwal B B. Curcumin is a non-competitive and selective inhibitor of phosphorylase kinase. FEBS Lett 1994; 341:19-22).

It has also been shown that suppression of phosphorylase kinase activity with curcumin leads to resolution of psoriasis (Heng M C Y et al. Drug-induced suppression of phosphorylase kinase activity correlates with resolution of psoriasis as assessed by clinical, histological and immunohistochemical parameters. British Journal of Dermatology 2000; 143:937-949).

Various pharmaceutical compositions as well as therapies for psoriasis have recently been disclosed, albeit none address the compositions comprising Tetrahydroxy curcumin//Bis-O-Demethyl curcumin (BDMC), curcumin, curcuminoids, which is unique and an important aspect of the present invention.

Therefore, there is a need in the art to develop herbal formulations which will also address the issues including inflammation and free radical generation in the mammals. Accordingly, the current application is directed to a nanoemulsified topical formulations comprising curcumin, tetrahydroxycurcumin//Bis-O-Demethyl curcumin (BDMC) or any other curcuminoids either alone or in combinations together with one or more pharmaceutically acceptable excipients or inactive ingredients suitable for the treatment of psoriasis as well as inflammation, which is a major component of diseases such as and not limiting to, acne, eczema, skin wounds, burns, smoking/nicotine-induced injury, premature aging, and sun-induced damage.

SUMMARY OF THE INVENTION

The current invention discloses a nanoemulsified topical formulation comprising curcumin, tetrahydroxycurcumin/Bis-O-Demethyl curcumin or curcuminoid either alone or in combinations together with one or more pharmaceutically, nutraceutically or dietically acceptable excipient(s) or inactive ingredients useful for treating oral disorders, inflammatory diseases such as Psoriasis, acne, eczema, skin wounds, burns, smoking/nicotine-induced injury, premature aging, and sun-induced damage and also mucositic disorders.

Further, the invention discloses a method for treating a mammal suffering from inflammatory disease conditions such as Psoriasis, acne, eczema, skin wounds, burns, smoking/nicotine-induced injury, premature aging, and sun-induced damage and mucositic disorders.

Further, the invention discloses a method for treating a mammal suffering from oral disorders such as, Halitosis, gingivitis, bad breath, dental caries and other diseases there of.

Various embodiments of the present invention relate to a nanoemulsified topical formulation useful for the treatment of inflammation, oral disorders and skin disorders, comprising an active ingredient selected from the group consisting of curcumin; bis-O-demethyl curcumin (BDMC); a mixture of curcumin, bis(demethoxy)curcumin, and demethoxycurcumin; and a mixture thereof; in combination with at least one pharmaceutically acceptable excipient or inactive ingredient. The active ingredient is present in an amount of 0.001% to 50% of the formulation, preferably in an amount of 0.01% to 30%, more preferably in an amount of 0.1% to 20%.

In various embodiments, the nanoemulsified topical formulation is a dosage form selected from the group consisting of semisolid dosage forms, ointments, creams, mouthwash, skin patches, toothpaste, gels, and lotions.

In various embodiments, the nanoemulsified topical formulation comprises particles of the active ingredient having a particle size in the range of 0.5 to 100 nm, preferably in the range of 1 to 50 nm, more preferably in the range of 2 to 25 nm. In various embodiments, the active ingredient comprises particles of curcumin having a particle size in the range of 0.5 to 100 nm. In some embodiments, the active ingredient comprises particles of bis-O-demethyl curcumin having a particle size in the range of 0.5 to 100 nm. In certain embodiments, the active ingredient comprises a mixture of at least two of:

particles of curcumin having a particle size in the range of 0.5 to 100 nm;

particles of bis-O-demethyl curcumin having a particle size in the range of 0.5 to 100 nm; and particles of a mixture of curcumin, bis(demethoxy)curcumin, and demethoxycurcumin having a particle size in the range of 0.5 to 100 nm.

Various embodiments are directed to a method for treating a subject, i.e., a mammal, suffering from a skin disorder, oral disorder or inflammation by topically treating the subject with an effective amount of a nanoemulsified formulation comprising an active ingredient selected from the group consisting of curcumin; bis-O-demethyl curcumin (BDMC); a mixture of curcumin, bis(demethoxy)curcumin, and demethoxycurcumin; and a mixture thereof; in combination with at least one pharmaceutically acceptable excipient or inactive ingredient. In various embodiments, the skin disorder is psoriasis, acne, eczema, skin wounds, burns, smoking/nicotine-induced injury, premature aging, and sun-induced damage, Mucositic disorders such as oral mucositis, oral wounds or oral abscesses.

In certain embodiments, the method treats inflammation through amelioration of at least one biomolecular marker selected from the group consisting of Tumor Necrosis Factor-α (TNF-α), Matrix MetalloProteinases (MMPs), Interleukins (IL), and Interferon Gamma (IFN γ); or inhibition of at least one enzyme selected from the group consisting of Protein Kinase C (PKC) and Phosphorylase Kinase.

DETAILED DESCRIPTION OF THE INVENTION

Figure 1:
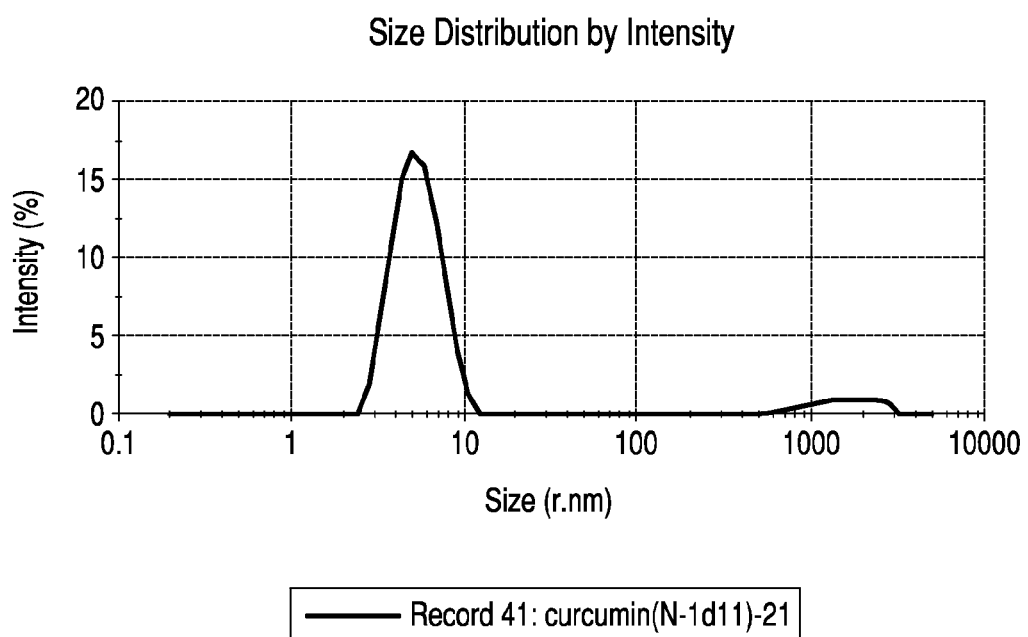
FIG. 1: The graph indicating the size of nano-emulsified curcumin 98%.

The invention will now be described in detail in connection with certain preferred and optional embodiments, so that various aspects thereof may be more fully understood and appreciated.

The term 'curcuminoid(s)' herein mentioned in the specification refers to a mixture of curcumin, demethoxycurcumin and bisdemethoxycurcumin.

The phrase 'compositions of the invention' herein mentioned in the specification refer to the compositions comprising 'curcumin' or 'tetrahydroxycurcumin' or 'curcuminoid' or 'in combinations thereof' and the same may be appreciated as such by the person skilled in the art.

In accordance with the above, in one aspect, tetrahydroxycurcumin or Bis-O-Demethyl curcumin (BDMC) has been used in the present invention to treat a range of skin problems including but not limited to psoriasis, acne, eczema, wounds, burns, photodamaged and photoaging skin. The nanoemulsified formulation comprising tetrahydroxycurcumin is useful as anti-inflammatory, anti-microbial and possibly also as anticarcinogenic. A process for producing tetrahydroxycurcumin or Bis-O-Demethyl curcumin is described in PCT Application No. PCT/IN05/00337, published as international patent publication WO/2007/043058, incorporated herein by reference.

Tetrahydroxycurcumin and Bis-O-Demethyl curcumin (BDMC) are, for the purposes of this specification, defined as being synonymous terms directed to the identical compound. The compound defined by the names tetrahydroxycurcumin and Bis-O-Demethyl curcumin has the structure:

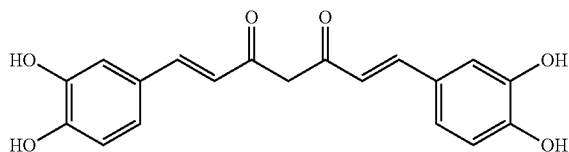 [SMILES: O=C(/C=C/c1ccc(O)c(O)c1)CC(=O)/C=C/c1ccc(O)c(O)c1]

Tetrahydroxycurcumin/Bis-O-Demethyl curcumin by amelioration of bimolecular markers such as Tumor Necrosis Factor (TNF)-α, Matrix Metallo Proteinases (MMPs), Interleukins, Interferon-γ (IFN γ) or by inhibiting the enzymes such as Protein Kinase (PKC), inhibiting phosphorylase kinase activity and possessing antioxidant activity, slows down the rapid epidermal turnover responsible for the poor quality stratum corneum in psoriasis, thus normalizing the epidermal barrier responsible for healthy skin and also in mucositic disorders.

In another aspect, curcumin, a naturally occurring product found in the spice, turmeric has been used in present invention to treat a range of skin problems including psoriasis, acne, eczema, wounds, burns, photodamaged photoaging skin and in mucositic disorders such as oral mucositis. The nanoemulsified formulation comprising curcumin is useful as anti-inflammatory, and possibly also as anticarcinogenic.

In a further aspect, the curcumin or tetrahydroxycurcumin may be replaced with curcuminoid to achieve the present invention to treat a range of skin problems including psoriasis, acne, eczema, wounds, burns, photodamaged and photoaging skin, all types of mucositic disorders.

In yet another embodiment, the invention discloses nanoemulsified formulation comprising curcumin and/or BDMC and/or curcuminoids as an anti-microbial, especially anti-bacterial agent for maintaining oral hygiene.

In yet another aspect, the invention discloses method of treating oral diseases including Halitosis, gingivitis, bad breath, dental caries and other diseases there of.

The nanoemulsified topical formulations of the present invention can be in the form but not limiting to semi solid dosage forms, ointment/cream/gel/lotions/skin patches/mouthwash/toothpaste may be inexpensive and can also be used as an effective complementary treatment in combination with one or more of the established treatments for inflammation, oral and skin disorders.

Tetrahydroxycurcumin has potent anti-inflammatory activity and hence may be beneficial in skin conditions which are caused due to inflammation like psoriasis, sun-damaged skin and acne, in addition, tetrahydroxycurcumin also suppresses phosphorylase kinase activity.

Thus, in an embodiment, the invention provides nanoemulsified topical formulations comprising tetrahydroxycurcumin (BDMC) as an anti-inflammatory, antioxidant and anti-bacterial agent useful in treating variety of skin and oral conditions.

In another embodiment, the invention provides nanoemulsified topical formulations comprising curcumin as an anti-inflammatory, anti-bacterial and antioxidant agent useful in treating variety of skin and oral conditions.

In yet another embodiment, the invention provides nanoemulsified topical formulations comprising curcuminoid as an anti-inflammatory, anti-bacterial and antioxidant agent together with pharmaceutically, nutraceutically or dietically acceptable or inactive ingredients s, useful in treating variety of skin and oral conditions.

In a further embodiment, the invention is directed to a method for treating psoriasis and all types of burns acne, skin wounds, eczema, the prevention and treatment of sun damaged skin, and the consequences of premature aging on the skin. The method comprises treating the affected skin, particularly, affected epidermis with the composition comprising curcumin or tetrahydroxycurcumin (BDMC) or any other suitable curcuminoid either alone or in combinations, in a quantity sufficient to detectably inhibit phosphorylase kinase activity.

Accordingly, the present invention discloses a nanoemulsified topical formulation comprising curcumin or tetrahydroxycurcumin or curcuminoid either alone or in combination together with one or more pharmaceutically, nutraceutically or dietically acceptable excipients or inactive ingredients useful in the treatment of skin and oral related disorders as described above.

Typically, curcumin or tetrahydroxycurcumin (BDMC) or curcuminoid is administered topically in the form including, but not limited to semi solid dosage forms, ointment/cream/gel/lotions/mouthwash/skin patches/toothpaste.

In another aspect, the invention provides curcumin or tetrahydroxycurcumin (BDMC) or cucuminoid alone or in combinations can be administered in a form, but not limiting to topical ointment/cream/mouthwash in the concentration of 0.001% to 50% preferrably 0.01% to 30% and more preferrably 0.1% to 20%

In another aspect, the curcumin or tetrahydroxycurcumin or curcuminoid used in the inventive composition, either alone or in combination, can be administered to the affected mammal 1 to 4 times daily or as prescribed by the physician depending on the severity of the condition. The mammal can be a human being, a dog, a cat, a cow, a horse, a sheep, a goat, or any another mammal.

In another aspect of the invention, the Nanoemulsified topical formulation as in the current invention, wherein the particle size of the curcumin/tetrahydroxy curcumin (BDMC) is in the range of 0.5 to 100 nm preferably 1 to 50 nm and more preferably 2 to 25 nm.

The particle size of the curcumin or tetrahydroxy curcumin or curcuminoid in the inventive formulation(s) is in the range of 8-11 nm.

In another aspect of the present invention, a method for treating inflammation in a mammal is provided, which comprises treating the mammal with the composition(s) of the invention by the amelioration of biomolecular markers such as Tumor Necrosis Factor (TNF)-α, Matrix Metallo Proteinases (MMPs), Interleukins, Interferon-γ (IFN γ) or by inhibiting the enzymes such as Protein Kinase (PKC), Phosphorylase Kinase In another aspect, the present invention provides a method for preventing or inhibiting proliferation and terminal differentiation of psoriatic epidermal cells, which comprises contacting the psoriatic epidermal cells with the composition(s) of the invention in a quantity sufficient to bring about the amelioration of biomolecular markers such as TNF-α, MMPs, Interleukins, IFN γ or by inhibiting the enzymes such as PKC, Phosphorylase Kinase The current inventors have developed a novel pharmaceutical composition for topical administration comprising curcumin or tetrahydroxycurcumin or curcuminoid either alone or in combination together with one or more pharmaceutically, nutraceutically or dietically acceptable inactive ingredients (s). The invention further discloses a novel method for prevention, treatment, or control of inflammation, as well as for the prevention, control, or treatment of inflammatory skin conditions such as Psoriasis, wounds, burns, acne, eczema, sun-induced damage, premature aging, and smoking/nicotine-induced damage.

Early development research has shown that a variety of inflammatory skin diseases and pathological conditions are associated with and worsened by the inflammatory process.

Although these mechanisms of injury are particular to psoriasis, similar mechanisms are likely to operate in the inflammation accompanying wounds, burns, acne, and eczema, as well as skin damage resulting from exposure to sunlight and tobacco smoke/nicotine. Thus, agents that bring about the amelioration of biomolecular markers such as TNF-α, MMPs, Interleukins, IFN γ or by inhibiting the enzymes such as PKC, Phosphorylase Kinase such as tetrahydroxycurcumin, curcumin or curcuminoids alone or in combination are likely to be effective in prevention, treatment or control of inflammation accompanying these aforementioned conditions.

The method comprises the step of treating the mammal affected with inflammation with curcumin or tetrahydroxycurcumin (BDMC) or curcuminoid either alone or in combination thereof, in a quantity sufficient by topical application The method of the present invention is effective in the prevention, treatment or control of inflammation through the aforementioned mode of action to bring about improvement in the affected epidermis, drying the lesions and in promoting healing and preventing recurrence of symptoms.

The dosages to be administered can be determined by one of ordinary skill in the art depending on the clinical severity of the disease, the age and weight of the patient, the exposure of the patient to conditions that may precipitate outbreaks of psoriasis or other dermatological or systemic inflammatory conditions, the degree of exposure to such conditions as sunlight or tobacco smoke, and other pharmacokinetic factors generally understood in the art, such as liver and kidney metabolism. Adjustments in the dosage regimen can be made to optimize the therapeutic response. Doses can be divided and administered on a daily basis or the dose can be reduced proportionally depending on the therapeutic situation.

In another embodiment, the excipients or inactive ingredients that can be used for preparing the composition(s) include but not limited to cream bases and emulsifiers such as light liquid paraffin, PEG, water washable bases such as cetyl alcohol, stearic acid, stearyl alcohol, glycerol monostearate, lanolin, glycerin and others and solid emulsifiers/nonionic surfactants such as Acconon, polyethylene glycol (PEG 200), glyceryl monosterate (GMS), polyethylene glycol (PEG 400) and Cetyl alcohol (CA) and Tween 80, preservatives such as methyl, ethyl or propyl parabens or bronidox, emollient such as Isopropyl myristate for ready absorption into the skin, collagen for maintaining the skin moisture and to give firmness, other flavoring agents such as lavender oil and antiseptic agents such as 2-phenyl ethanol In another aspect, the composition comprises the inclusion of Niacinamide in the topical formulation of the present invention for beneficial synergistic result in reducing the red blotchiness and hyper pigmentation of skin.

In another aspect, the composition(s) can also include but not limited to known pharmaceutically, nutraceutically or dietically acceptable antiinflammatory, antipsoriatic, antioxidant, anti allergic, antiviral, antibacterial and antiangiogenic agents.

In another embodiment, the curcumin or tetrahydroxycurcumin or curcuminoid either alone or in combination, can be formulated by techniques including but not limited to nanoemulsification which can be carried out by methods such as sonication/emulsification/titration, milling, spray drying, solid dispersion, hot-melt extrusion, freeze drying method by techniques A method for preparing the nanoemulsion of tetrahydroxycurcumin is described in example 1, however, the nanoemulsion curcumin and curcuminoid can also be prepared in a similar process.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Nanoemulsified Topical Formulation Comprising Tetrahydroxycurcumin

100 gms of Cream

Glyceryl Monosterate (GMS)—5.28 gm, Polyethylene glycol 4000 (PEG 4000)—2.64 gm, Dimethyl sulfoxide (DMSO)—1 ml, Niacinamide 100 mg, Iso Propyl Myristate 4 ml, Phenyl 2-ethanol (1 ml), Light Liquid paraffin 2 ml, Cetyl alcohol 2.64 gins, Phenyl 2 ethanol 1 ml, Collagen 13.20 gms, tetrahydroxycurcumin 250 mg, Bronidox 100 μl, lavender oil 100 μl and demineralised water 65.04 ml.

Manufacturing procedure comprises the following steps:
1. transferring the weighed amounts of glyceryl monosterate (GMS), polyethylene glycol (PEG400), cetyl alcohol (CA) into a clean 50 ml beaker, followed by pipetting out light liquid paraffin and Iso propyl myristate into the emulsifiers;
2. adding Phenyl-2-Ethanol to the above mixture;
3. soaking collagen in 10 ml of demineralised water till the solution becomes clear (~25 min) followed by adding niacinamide to it.
4. transferring the weighed quantity of tetrahydroxycurcumin/curcumin/curcuminoids into a clean container and solubilized into a nanoemulsion by mixing with Tween 80 and PEG400 and sonicating it under controlled temperature.
5. melting the solid emulsifiers, glyceryl monosterate (GMS), polyethylene glycol (PEG 400) and Cetyl alcohol (CA), at 70° C., and heating simultaneously demineralized water;
6. adding immediately half of the solubilized tetrahydroxycurcumin into the hot emulsifiers and mixing thoroughly;
7. Simultaneously heating 65.04 ml of demineralised water at 70° C.;
8. adding the molten emulsifiers into the boiled demineralised water and mixing with vigorous stirring till it attains cream consistency at the room temperature;
9. adding collagen and niacin mixture and mix well to form a smooth cream;
10. adding another half the amount of solubilized tetrahydroxycurcumin to the cooled cream and mixing the mixture.
11. dissolving and adding Bronidox in 1 ml of PEG 400 to the mixture of step 9; and
12. adding lavender oil to the above cream for fragrance.

Example 2

Solubulization of Curcumin

1) 60 mg curcumin was weighed into a 10 ml beaker
2) To this 1 g (765 ul) Tween80 and 1 g PEG was added and stirred well using a glass rod.
3) Following this the tube was sonicated for 30 min or till the curcumin is completely solubulized.
4) A deep red colour solution was formed.
5) The particle size distribution studies reported the size to be within 8-11 nm in the nanoemulsion which was found to be highly acceptable for a nanoemulsion

Example 3

Particle Size Distribution Data for Nanoemulsified Curcumin 98% and Bis-O Demethyl Curcumin BDMC

A Particle size distribution study conducted on the nanoemulsified formulation has further confirmed that the curcumin molecules exist as nano sized particles in the current formulation. This study proves that a curcumin molecule which is originally 374 nm in the unformulated form is emulsified into 8-11 nm sized particles through a unique process, which has been indicated for this enhanced transport and efficacy of curcumin through the formulation.

The study was conducted using Malvern particle size analyzer. The map of scattering intensity versus angle is the primary source of information used to calculate the particle size. The scattering of particles is accurately predicted by the Mie scattering model allowing accurate sizing across the widest possible dynamic range. During the laser diffraction measurement, particles are passed through a focused laser beam. These particles scatter light at an angle that is inversely proportional to their size. The angular intensity of the scattered light is then measured by a series of photosensitive detectors. The advantage of this study is that there is no sample preparation involved.

Figure 2:
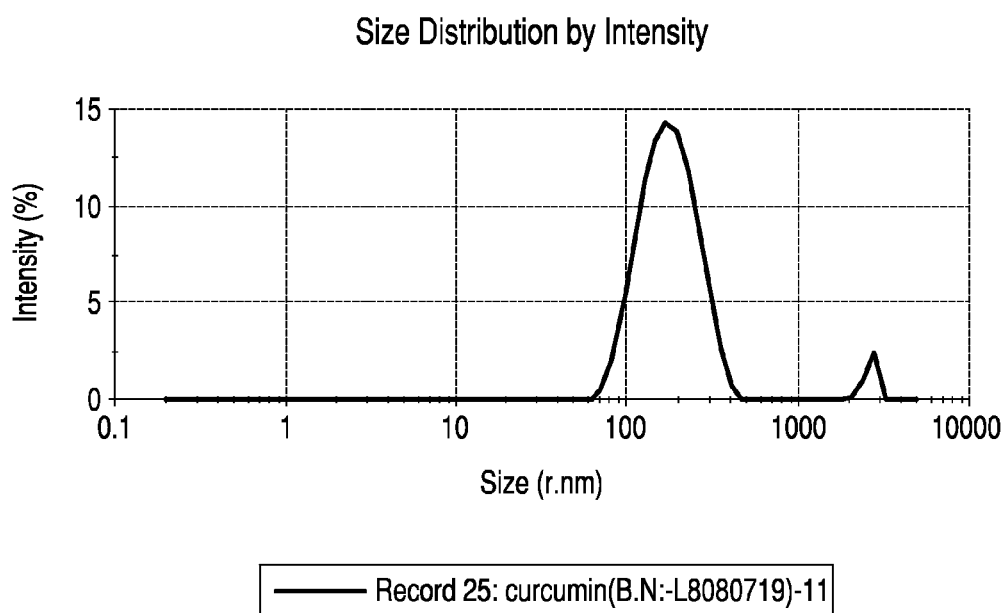
FIG. 2: The graph indicating the size of unformulated curcumin 98%.
Figure 3:
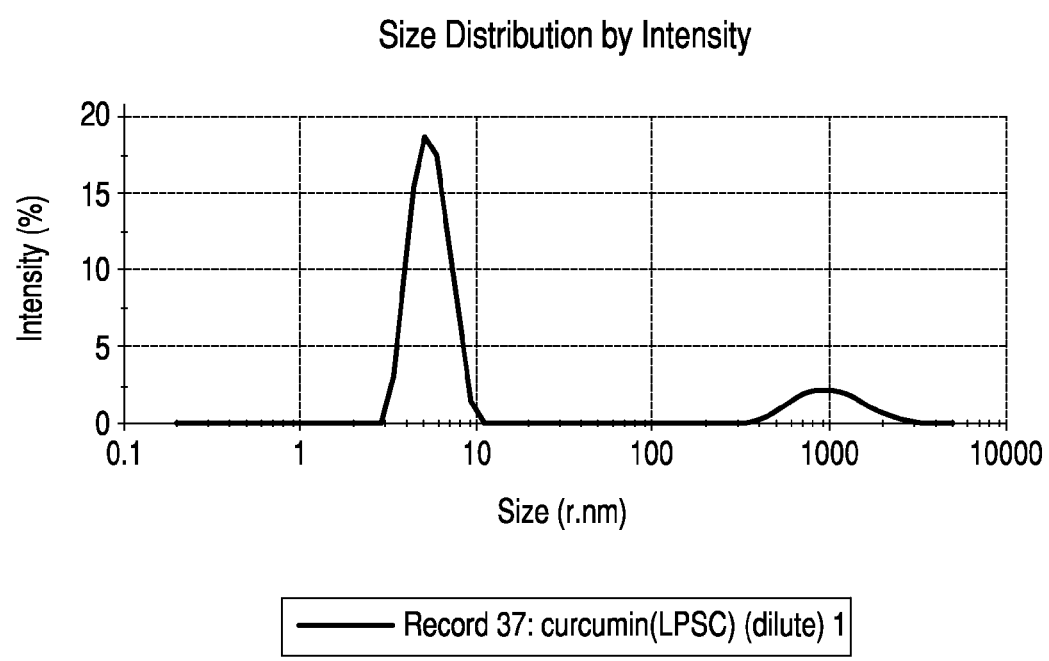
FIG. 3: The graph indicating the size of nano-emulsified BDMC.

The study conducted on the particle size distribution of nanoemulsified curcumin 98% and nanoemulsified BDMC and curcumin 98% clearly showed the particle sizes of the nanoemulsified BDMC and curcumin 98% was between 8-11 nm, (as described in FIGS. 1-3), which is the ideal size of a nano-emulsified compound when compared to the particle size of unformulated curcumin 98% which was 373 nm. Additional peaks can be observed which is contributed by the high molecular weight excipients used to prepare the formulation. The results obtained demonstrate that the current formulations are in nanoemulsified form

Example 4

Study on the Efficacy of Nanoemulsified Curcumin Composition in the Induction of Orthokeratosis in Balb/c Mice by Mouse Tail Test

In vivo studies were performed to measure the antipsoriatic activity of a novel curcumin formulation, utilizing a standard, sensitive and reproducible mouse-tail test method for a quantitative evaluation of the effect of the drug on epithelial differentiation and induction of orthokeratosis (granular layer) [Bosman et al., 1992; Mitra et al., 1998], according to which, the histology of the mouse tail is comparable to the histopathology of the psoriatic human skin.

Forty animals (Balb/C mice) in the age group of 8 to 9 weeks were used for this study, comprising of five groups with 8 animals in each group. The designated dose of test substance was topically applied to the mouse tail twice daily for 14 days according to the respective groups assigned (100 mg of the novel curcumin formulation—the study article or 100 μl of solubilised curcumin or 100 μl of 5% coal tar as positive control or drug vehicle alone) and an untreated mice tail served as a naïve control. At the end of the experimental period the mice were sacrificed. The treated section of tail, approximately 2.5 cm in length, was removed and fixed in 4% formalin. Longitudinal histological sections (10 sections per tail) from the treated tail and untreated control were prepared and Hematoxylin and Eosin (H&E) stained.

The horizontal length of the fully developed granular layer within an individual scale in relation to its total length was measured microscopically. The percentage ratio of the horizontal length of the fully developed granular layer within an individual scale divided by the horizontal length of that particular scale was calculated to arrive at the degree of orthokeratosis induced. The calculated mean of the values obtained in the individual animals, was subject to statistical analysis and it was inferred that, the treatment with the novel formulation of curcumin and the plain solubilised curcumin showed significant improvement in the induction of the orthokeratotic layer and formation of the continuous granular and in epidermal layer thickening. The positive results obtained in the study groups were found to be comparable to the standard conventional coal tar therapy and significantly higher than the vehicle control as is evidenced from FIGS. 4 to 8.

Figure 4:
FIG. 4: Histopathology indicating T.S of the mouse tail (control group)
Figure 5:
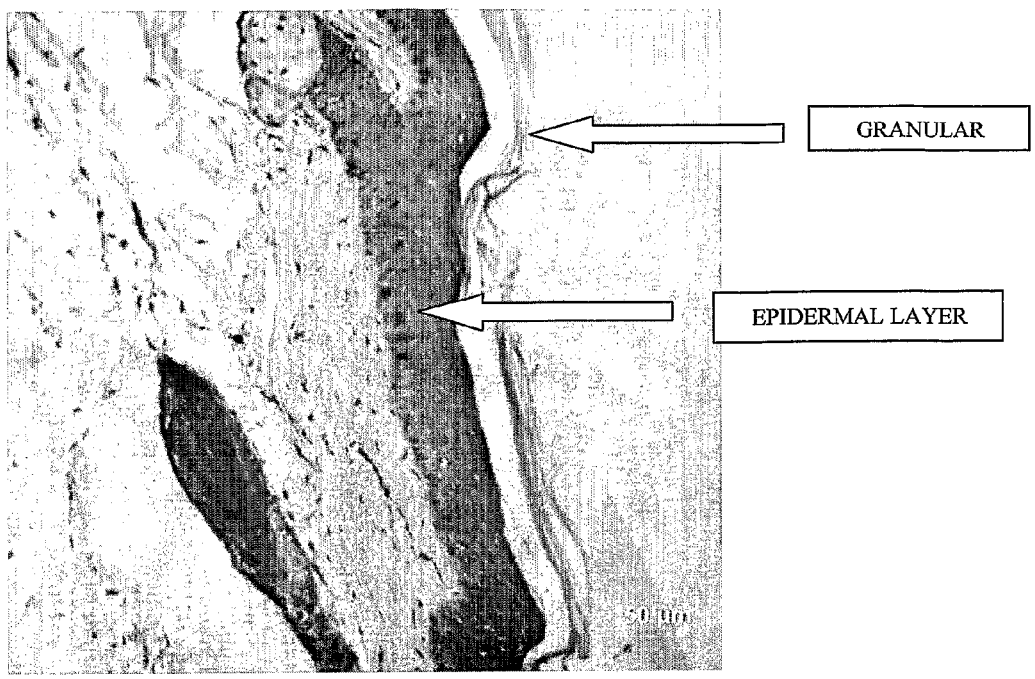
FIG. 5: Histopathology indicating T.S of the mouse tail (vehicle group)
Figure 6:
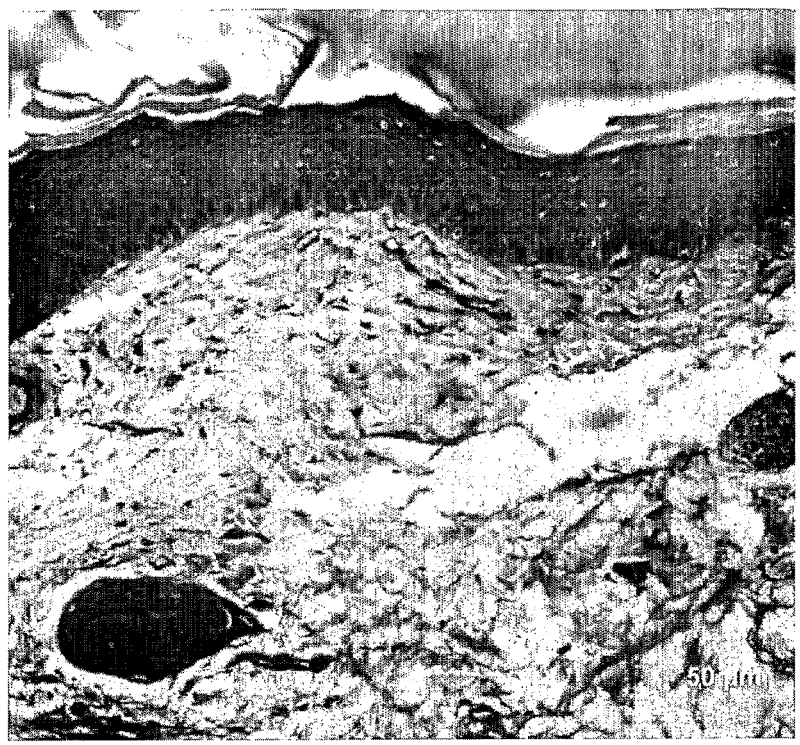
FIG. 6: Histopathology indicating T.S of the mouse tail treated with Coal tar
Figure 7:
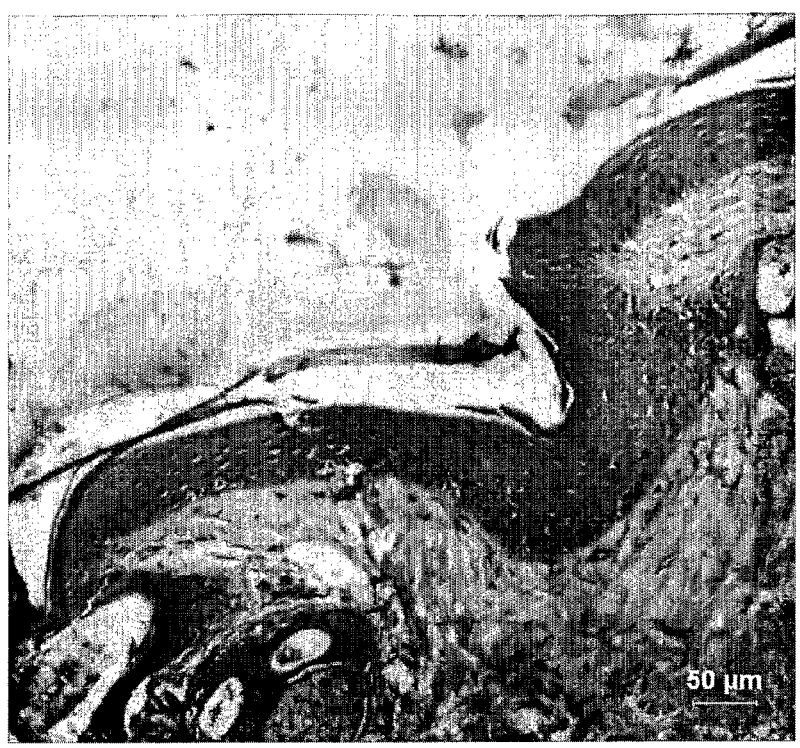
FIG. 7: Histopathology indicating T.S of the mouse tail treated with solubilised curcumin
Figure 8:
FIG. 8: Histopathology indicating T.S of the mouse tail treated with formulated curcumin
Figure 9:
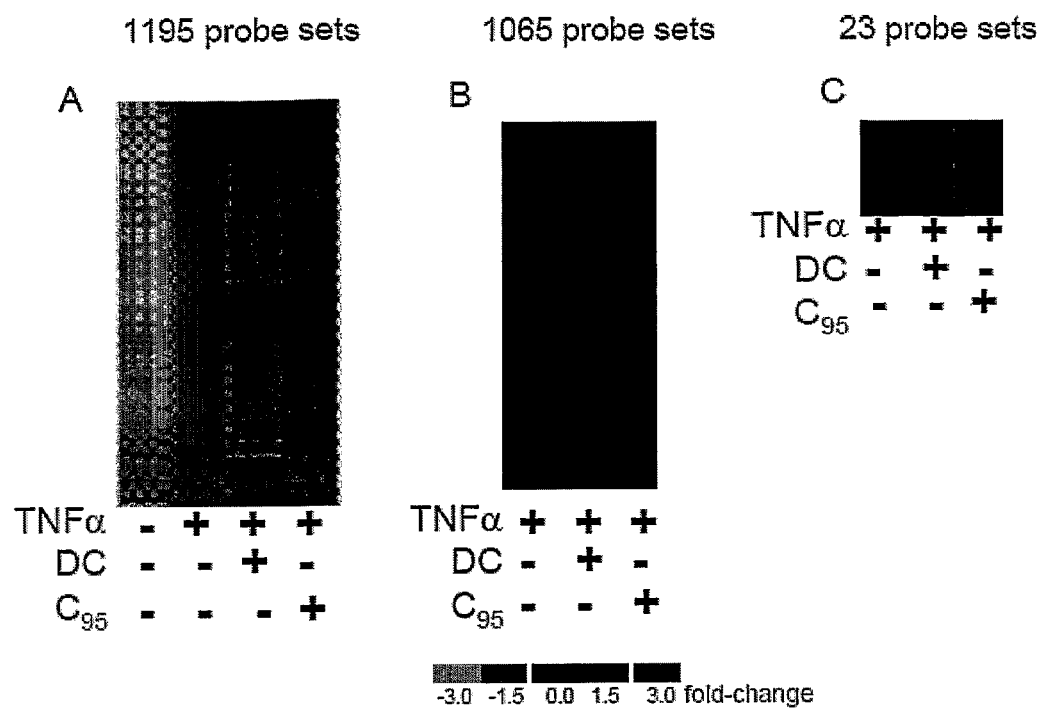
FIG. 9: Studies showing Genes that were >2.0 fold up regulated in TNFα-treated group compared to TNFα untreated control group were selected and subjected to hierarchical clustering (FIG. 9A). Major clusters of genes that were up-regulated following TNFα treatment but were down regulated uniquely by BDMC/curcumin/curcuminoids were selected as DC (FIG. 9B) or C95 sensitive genes (FIG. 9C)

FIG. 4 shows T.S of the mouse tail (control group) observed for Histopathology and read under microscope shows a discontinuous Granular layer and a weakly formed epidermal layer as characterized in human psoriatic lesions. FIG. 5 shows a discontinuous formation of granular layer and a fairly developed epidermal layer in the vehicle treated group (containing waxes). FIG. 6 shows a well developed epidermal layer in this coal tar treated group. The granular layer formation is also well defined in this case. Coal tar is normally used in the management of psoriasis. Therefore, herein used as a reference standard for comparing the efficacy of the formulated curcumin. FIG. 7 shows the formation of well defined epidermal layer in case of solubilised curcumin. This was prepared with plain curcumin solubilized in excipients. However, in this the granular layer is not continuous. FIG. 8 shows a continuous granular layer and a good epidermal thickness with the treatment of the formulated curcumin. The effect is comparable to that of coal tar.

The clinical outcome of the above study clearly suggests the potential therapeutic use of the composition of the invention in treating psoriasis and related inflammatory conditions.

Example 5

Microarray Studies Conducted on BDMC/Curcumin/Curcuminoids

TNFα has been implicated and found to be associated with the pathogenesis of several clinical conditions involving inflammatory process and more specifically to the immune altering function of several chronic conditions like Psoriasis, Atherosclerosis, Diabetes Mellitus type II, Sepsis and Rheumatoid arthritis.

TNFα and its receptors play an important role in the development and persistence of psoriatic plaques. TNFα is found to be upregulated in psoriatic condition (skin and synovium) and also represents prominent target in the treatment of psoriasis.

Figure 10:
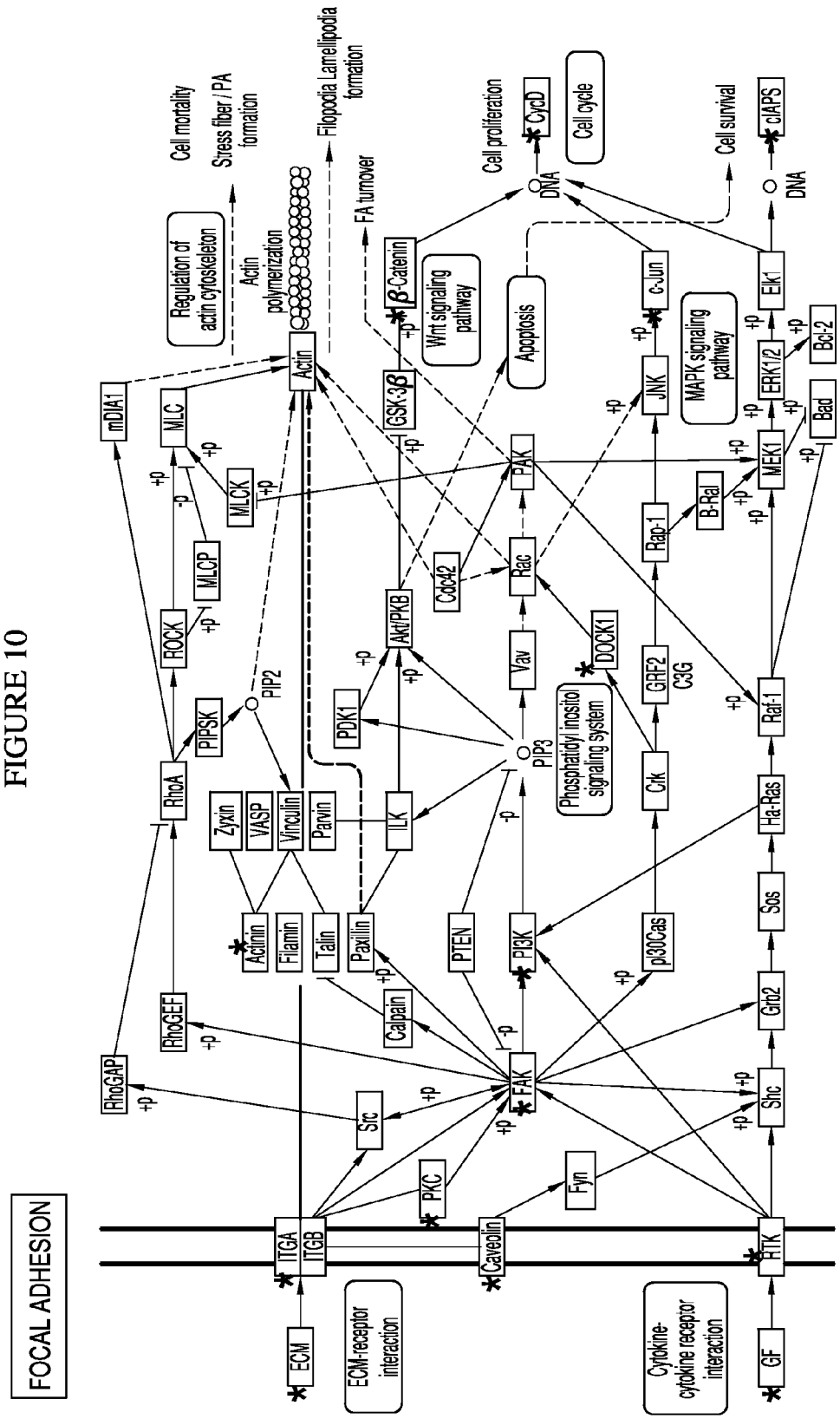
FIG. 10: Candidate genes identified through functional analysis using DAVID (Database for Annotation, Visualization and Integrated Discovery NIAID, NIH) (focal adhesions).
Figure 11:
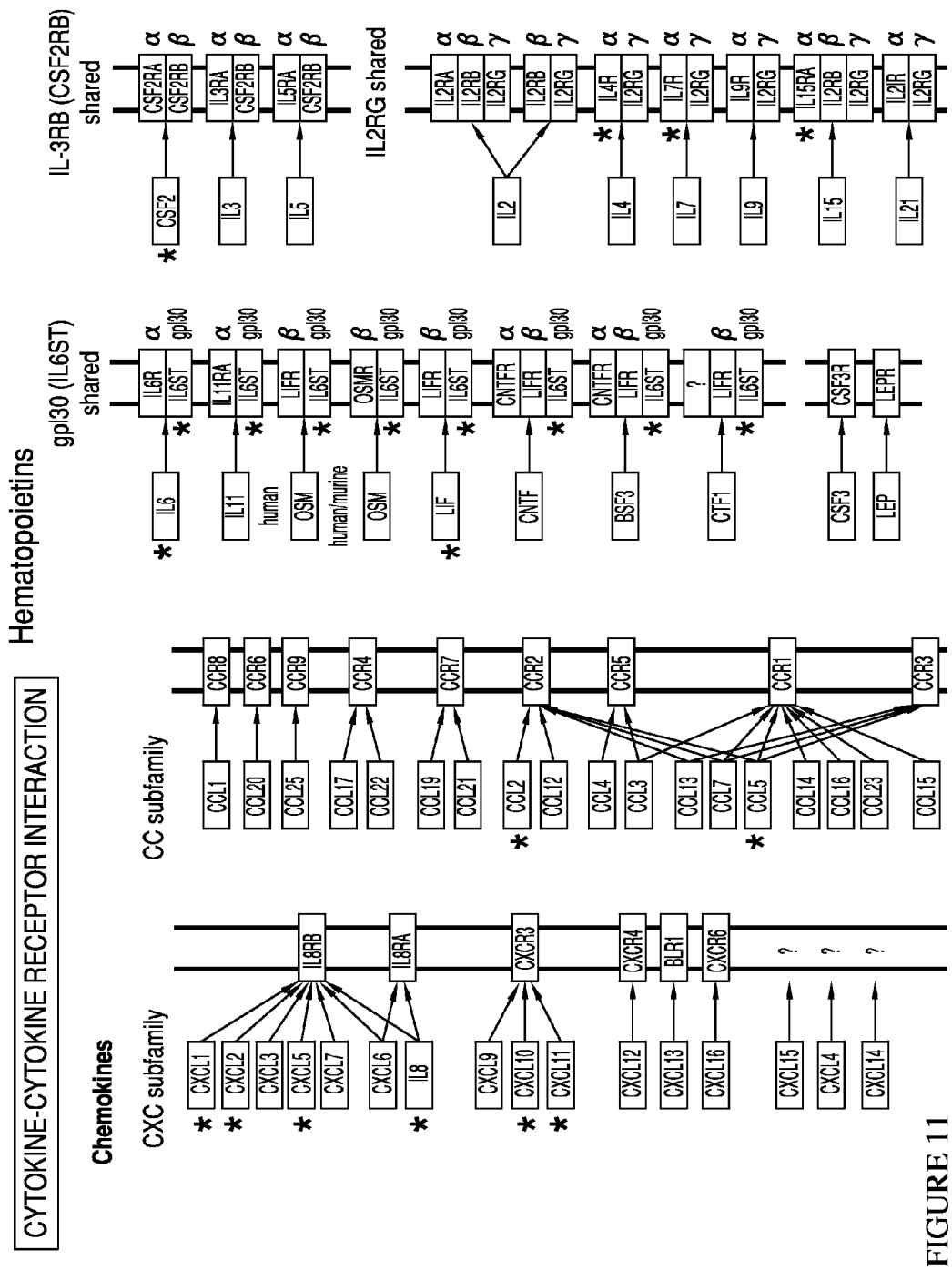
FIG. 11: Candidate genes identified through functional analysis using DAVID (Database for Annotation, Visualization and Integrated Discovery NIAID, NIH)

Effects of BDMC/Curcumin/Curcuminoids were Studied in TNFα-Induced Gene Expression in Human Microvascular Endothelial Cells (HMEC):

Micro array analysis was carried out to identify the sets of gene differentially expressed in TNFα treated endothelial cells pretreated/not pretreated with demethylated curcuminoids (BMDC, curcumin)/with curcuminoids. Data acquisition and image processing were performed using GCOS (Gene Chip Operating Software, Affymetrix). Genes that were >2.0 fold up regulated in TNFα-treated group compared to TNFα untreated control group were selected and subjected to hierarchical clustering. Major clusters of genes that were up-regulated following TNFα treatment but were down regulated uniquely by demethylated curcuminoids (BMDC, curcumin)/curcuminoids were selected as sensitive genes. These sub-clusters were subjected to further functional analysis using DAVID (Database for Annotation, Visualization and Integrated Discovery NIAID, NIH) (FIG. 10, 11). Major known pathways (KEGG, Kyoto Encyclopedia of Genes and Genomes) identified in each of the cluster have been illustrated as pathway maps marking the candidate genes.

The data generated, relates to the activity of bis-O-demethyl curcumin against the functions of TNFα as discussed.

GeneChip™ screening of TNFα-inducible transcriptome of HMEC identified 1195 probe sets that were induced by a magnitude of two-fold or higher.

The microarray studies conducted, as aforementioned, have shown that in microvascular endothelial cells challenged with TNFα, in total, 1065 TNFα. inducible genes were sensitive to bis-O-demethyl curcumin (FIG. 1). It has also been studied that bis-O-demethyl curcumin had antagonizing effects on TNFα.

Therefore the antagonizing effect of bis-o-demethyl curcumin against TNFα and subsequently on the down regulation of TNFα mediated mechanisms can be well applied in the treatment of psoriasis.

We claim:

1. A topical formulation useful for the treatment of inflammation, skin disorders and oral disorders comprising:
   a composition comprising at least one emulsifier or non-ionic surfactant as a solvent; and nanosized particles of at least one component selected from the group consisting of curcumin; bis-O-demethyl curcumin (BDMC); and a mixture of curcumin, bis(demethoxy)curcumin, and demethoxycurcumin; and
   at least one pharmaceutically acceptable excipient or inactive ingredient;
   wherein said nanosized particles have a mean particle size of between 1 nm and 50 nm, wherein at least 68% of said nanosized particles have a particle size between 1 nm and 50 nm.

2. The topical formulation as claimed in claim 1, wherein said formulation comprises said at least one component in an amount of 0.001% to 50%.

3. The topical formulation as claimed in claim 2, wherein said formulation comprises said at least one component in an amount of 0.01% to 30%.

4. The topical formulation as claimed in claim 3, wherein said formulation comprises said at least one component in an amount of 0.1% to 20%.

5. The topical formulation as claimed in claim 1, wherein said formulation is a dosage form selected from the group consisting of semisolid dosage forms, ointments, creams, gels, lotions, skin patches, mouthwash and toothpaste.

6. The topical formulation as claimed in claim 1, wherein at least 95% of said nanosized particles have a particle size between 1 nm and 50 nm.

7. The topical formulation as claimed in claim 6, wherein said at least one component comprises particles having a mean particle size in the range of 2 to 25 nm.

8. The topical formulation as claimed in claim 1, wherein said at least one component comprises particles of curcumin having a mean particle size in the range of 1 nm to 50 nm.

9. The topical formulation as claimed in claim 1, wherein said at least one component comprises particles of bis-O-demethyl curcumin having a particle size in the range of 1 nm to 50 nm.

10. The topical formulation as claimed in claim 1, wherein said at least one excipient or inactive ingredient is selected from the group consisting of:
    i) cream bases and emulsifiers selected from the group consisting of light liquid paraffin and PEG;

ii) water washable bases selected from the group consisting of cetyl alcohol, stearic acid, stearyl alcohol, glycerol monostearate, lanolin, and glycerin;

iii) solid emulsifiers or nonionic surfactants selected from the group consisting of glyceryl monosterate (GMS), Acconon, polyethylene glycol (PEG 200), polyethylene glycol (PEG 400), cetyl alcohol (CA), and Tween 80;

iv) preservatives selected from the group consisting of methyl, ethyl or propyl parabens and bronidox;

v) emollients;

vi) collagen;

vii) flavoring agents; and viii) antiseptic agents.

11. The topical formulation as claimed in claim 1, further comprising Niacinamide.

12. The topical formulation as claimed in claim 1, further comprising at least one additional active agent selected from the group consisting of antiinflammatory agents, antipsoriatic agents, antioxidant agents, anti allergic agents, antiviral agents, antibacterial agents, anti-mucositic and antiangiogenic agents.

13. A method for treating a subject suffering from an oral disorder, skin disorder or inflammation, wherein said method comprises topically treating the subject with an effective amount of a topical formulation as claimed in claim 1.

14. The method as claimed in claim 13, wherein said subject is a mammal.

15. The method as claimed in claim 13, wherein said skin disorder is selected from the group consisting of psoriasis, acne, eczema, skin wounds, burns, smoking/nicotine-induced injury, premature aging, and sun-induced damage, Mucositic disorders such as oral mucositis, oral wounds and oral abscesses.

16. A method as claimed in claim 13, wherein said oral disorders include Halitosis, gingivitis, bad breath, dental caries, mouth ulcerative, tissue necroses, and other oral diseases.

17. The method as claimed in claim 13, wherein said method treats inflammation through:

a) amelioration of at least one biomolecular marker selected from the group consisting of Tumor Necrosis Factor-$\alpha$ (TNF-$\alpha$), Matrix MetalloProteinases (MMPs), Interleukins (IL), and Interferon Gamma (IFN $\gamma$); or b) inhibition of at least one enzyme selected from the group consisting of Protein Kinase C (PKC) and Phosphorylase Kinase.

18. A topical formulation useful for the treatment of inflammation, skin disorders and oral disorders comprising:

nanosized particles comprising at least one component selected from the group consisting of curcumin; bis-O-demethyl curcumin (BDMC); and a mixture of curcumin, bis(demethoxy)curcumin, and demethoxycurcumin; and at least one pharmaceutically acceptable excipient or inactive ingredient;

said nanosized particles being prepared by mixing said at least one component with at least one emulsifier or nonionic surfactant as a solvent to form a mixture, and sonicating the mixture to form nanosized particles.

19. A method of making a topical formulation, comprising:

mixing at least one curcuminoid component with at least one emulsifier or nonionic surfactant as a solvent to form a mixture, said curcuminoid component being selected from the group consisting of curcumin; bis-O-demethyl curcumin (BDMC); and a mixture of curcumin, bis (demethoxy)curcumin, and de methoxycurcumin;

sonicating the mixture of said at least one curcuminoid component and said at least one emulsifier or nonionic surfactant to form a nanosized particles; and adding the sonicated mixture to a topically acceptable medium.

20. The method of claim 19, wherein said topically acceptable medium is a topically acceptable aqueous medium.

21. The method of claim 19, wherein said topically acceptable medium is a topically acceptable nonaqueous medium.

* * * * *